US011013493B2

(12) United States Patent
Romano et al.

(10) Patent No.: US 11,013,493 B2
(45) Date of Patent: *May 25, 2021

(54) SYSTEM AND METHOD FOR STERILE SHEATHING OF A MEDICAL PROBE

(71) Applicants: THE GENERAL HOSPITAL CORPORATION, Boston, MA (US); MASSACHUSETTS INSTITUTE OF TECHNOLOGY, Cambridge, MA (US)

(72) Inventors: J. Jordan Romano, Boston, MA (US); Elizabeth N. Bearrick, Cambridge, MA (US); Lauren R. Hernley, Cambridge, MA (US); Saul A. Lopez, Los Angeles, CA (US); Laura M. Tanenbaum, Cambridge, MA (US); Marcel A. C. Thomas, Cambridge, MA (US); Teddy A. Toussaint, Cambridge, MA (US)

(73) Assignees: Massachusetts Institute of Technology, Cambridge, MA (US); THE GENERAL HOSPITAL CORPORATION, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/106,423

(22) Filed: Aug. 21, 2018

(65) Prior Publication Data
US 2019/0029641 A1 Jan. 31, 2019

Related U.S. Application Data

(63) Continuation of application No. 14/215,269, filed on Mar. 17, 2014, now Pat. No. 10,085,716.
(Continued)

(51) Int. Cl.
A61B 8/00 (2006.01)
A61B 50/20 (2016.01)
(Continued)

(52) U.S. Cl.
CPC .......... A61B 8/4422 (2013.01); A61B 8/4281 (2013.01); A61B 46/10 (2016.02);
(Continued)

(58) Field of Classification Search
CPC .............. A61B 1/00144; A61B 8/4422; A61B 2562/242; A61B 2562/247;
(Continued)

(56) References Cited

U.S. PATENT DOCUMENTS 4,275,812 A  6/1981  Poncy et al.
4,383,692 A  5/1983  Proctor
(Continued)

FOREIGN PATENT DOCUMENTS

WO   WO03082174 A1   10/2003

OTHER PUBLICATIONS

Koibuchi et al., "Comparison of methods for evaluating bacterial contamination of ultrasound probes", Japan Society of Ultrasonics in Medicine, 2009, p. 187-192, No. 36, Springer.
(Continued)

Primary Examiner — Matthew P Travers
(74) Attorney, Agent, or Firm — Intrinsic Law Corp.

(57) ABSTRACT

An apparatus and a method for sheathing a medical device, tool, instrument or probe (generally, probe) is provided. Among other aspects, a probe support jig capable of supporting the probe is provided, which includes a mechanical coupling for accepting a sheath on a sheath shell. In use, the sheath shell is coupled at one end thereof to the support jig
(Continued)

and the probe is fed into the sheath, which is coupled to the sheath shell at another end thereof.

28 Claims, 10 Drawing Sheets

Related U.S. Application Data

(60) Provisional application No. 61/788,727, filed on Mar. 15, 2013, provisional application No. 61/834,999, filed on Jun. 14, 2013.

(51) Int. Cl.
*A61B 46/10* (2016.01)
*A61B 1/00* (2006.01)
*A61N 7/00* (2006.01)

(52) U.S. Cl.
CPC .............. *A61B 50/20* (2016.02); *A61N 7/00* (2013.01); *A61B 1/00142* (2013.01); *A61B 2562/242* (2013.01); *A61B 2562/247* (2013.01); *Y10T 29/49817* (2015.01); *Y10T 29/53961* (2015.01)

(58) Field of Classification Search
CPC .............. A61B 46/13–17; A61B 50/20; A61B 1/00142; A61B 6/4423; A61B 46/10
See application file for complete search history.

(56) References Cited

U.S. PATENT DOCUMENTS

| | | |
|---|---|---|
| 4,593,699 A | 6/1986 | Poncy et al. |
| 4,783,950 A | 11/1988 | Santagati |
| 4,815,470 A | 3/1989 | Curtis et al. |
| 4,827,695 A | 5/1989 | Logan |
| 4,858,821 A * | 8/1989 | Bickelhaupt ....... A61B 1/00144 229/123.1 |
| 4,877,033 A | 10/1989 | Seitz, Jr. |
| 4,984,582 A | 1/1991 | Romaniszyn et al. |
| 4,997,084 A | 3/1991 | Opie et al. |
| 5,100,018 A | 3/1992 | Rosati et al. |
| 5,195,659 A | 5/1993 | Eiskant |
| 5,259,383 A | 11/1993 | Holstein et al. |
| 5,316,019 A | 5/1994 | Jones |
| 5,410,888 A | 5/1995 | Kaiser et al. |
| 5,450,706 A | 9/1995 | Latini et al. |
| 5,451,203 A | 9/1995 | Lamb |
| 5,474,201 A | 12/1995 | Liu |
| 5,490,522 A | 2/1996 | Dardel |
| 5,492,247 A | 2/1996 | Shu et al. |
| 5,507,295 A | 4/1996 | Skidmore |
| 5,695,450 A | 12/1997 | Yabe et al. |
| 5,910,113 A | 6/1999 | Pruter |
| 5,941,889 A | 8/1999 | Cermak |
| 6,039,694 A | 3/2000 | Larson et al. |
| 6,117,085 A | 9/2000 | Picatti et al. |
| 6,205,352 B1 | 3/2001 | Carroll |
| 6,217,518 B1 | 4/2001 | Holdaway et al. |
| 6,379,307 B1 | 4/2002 | Filly et al. |
| 6,402,695 B1 | 6/2002 | Grimm |
| 6,561,389 B1 | 5/2003 | Earle |
| 6,582,368 B2 | 6/2003 | Holdaway et al. |
| 6,855,861 B2 | 2/2005 | Dotta |
| 7,160,246 B2 | 1/2007 | Humble et al. |
| 7,299,951 B2 | 11/2007 | Jahnke et al. |
| 7,790,183 B2 | 9/2010 | Darouiche et al. |
| 7,850,602 B2 | 12/2010 | Humble et al. |
| 7,939,152 B2 | 5/2011 | Haskin et al. |
| 7,942,060 B2 | 5/2011 | Suri et al. |
| 8,012,094 B2 | 9/2011 | Prager et al. |
| 8,166,975 B2 | 5/2012 | Morgan |
| 10,085,716 B2 * | 10/2018 | Romano .............. A61B 8/4422 |
| 2001/0000672 A1 | 5/2001 | Ooshima et al. |
| 2006/0222052 A1 | 10/2006 | Harr et al. |
| 2007/0233031 A1 | 10/2007 | Benson et al. |
| 2008/0029101 A1 | 2/2008 | Abadi et al. |
| 2008/0139944 A1 | 6/2008 | Weymer et al. |
| 2009/0226541 A1 | 9/2009 | Scholz et al. |
| 2009/0255221 A1 | 10/2009 | Lyman, Jr. |
| 2011/0186594 A1 | 8/2011 | Parker |
| 2011/0208007 A1 | 8/2011 | Shohat et al. |
| 2011/0275891 A1 | 11/2011 | Shemi |
| 2011/0297163 A1 | 12/2011 | Gharib |
| 2011/0301459 A1 | 12/2011 | Gharib |

OTHER PUBLICATIONS

C. Moore, "Ultrasound-Guided Procedures in Emergency Medicine", Ultrasound Clin, 2011, p. 277-289, No. 6, Elsevier Inc.
Sheathing Technologies, Inc., "Pre-Gelled Ultrasonic Probe Covers—Ready to Use: A Complete Line of Rolled, Latex-Free Probe Covers for Vaginal & Rectal Procedures", Sheathing Technologies, Inc., Morgan Hill, CA.
"Sensis Condom", www.amazon.com/s/ref=bl_sr_hpc?_encoding=UTF8&node=3760901&field-brandtextbin=Sensis.
Jimenez et al., "Sheathing of the Endovaginal Ultrasound Probe: Is It Adequate?", Infectious Diseases in Obstetrics and Gynecology, 1993, p. 37-39, vol. 1, Wiley-Liss, Inc.
Machi et al., "Technique of ultrasound examination during laparoscopic cholecystectomy", Surgical Endoscopy, 1993, p. 544-549, vol. 7, Springer-Veriag New York Inc.

* cited by examiner

SYSTEM AND METHOD FOR STERILE SHEATHING OF A MEDICAL PROBE

RELATED APPLICATIONS

The present application is a continuation of U.S. patent application Ser. No. 14/215,269, entitled "System and Method for Sterile Sheathing of a Medical Probe", filed on Mar. 17, 2014, and claims the benefit and priority of U.S. Provisional Application No. 61/788,727, entitled "Ultrasound Probe Sheathing Device," filed on Mar. 15, 2013, and U.S. Provisional Application No. 61/834,999, also entitled "Ultrasound Probe Sheathing Device," filed on Jun. 14, 2013, all of which are hereby incorporated by reference.

GOVERNMENT SUPPORT

This invention was made with government support under Cooperative Agreement W81XWH-09-2-0001 awarded by CIMIT under U.S. Army Medical Research Acquisition Activity. The U.S. Government has certain rights in the invention.

TECHNICAL FIELD

The present application relates to application of a sterile sheath over a medical tool such as an ultrasound probe for use in a medical procedure.

BACKGROUND

It is important to maintain a sterile environment in situations where patient medical treatment can lead to complications from infection or non-sterile practices, especially in invasive diagnostic or therapeutic applications. One example where sterile practices and equipment are required is in the introduction of medical instruments, tools, diagnostic and therapeutic probes and similar devices (collectively referred to herein as "probes"), such as ultrasonic probes, which come in contact with a patient's body.

Conventional methods for sheathing a probe include application of a sterile sheath, for example a thin plastic film or condom, over the probe prior to placement of the probes on the patient's body or to a vulnerable sterile area. However, conventional methods for applying the sheath to the probe, and handling of the sheathed probe are less than ideal. For example, conventional methods and systems usually require more than one person to simultaneously handle the probe and apply the sheath to the probe. Also, conventional ways of sheathing a probe are prone to errors defeating the intended sterility of the probes and sheaths. In addition, wasted time in the clinical setting due to inefficient or ineffective applications of sheaths to probes results in wasted materials and in lost revenue for the medical institution or practice and reduced patient care opportunities, not to mention added health care costs to patients and society.

FIG. 1 illustrates a simplified non-sterile conventional setup 10 for sheathing a medical probe. A flexible sheath, such as an elongated furled sock, bag, condom or similar sheathing article 100 is held in one hand so as to form a depression, cavity or pocket-like recess therein 102. An amount of coupling gel 110 such as ultrasound coupling gel is dispensed from a gel packet or bottle 120. The gel facilitates the propagation of imaging or therapeutic energy waves (e.g., ultrasound) therethrough by eliminating air pockets between the active probe tip inserted into pocket 102 and the sheath 100, and by providing an impedance matched medium for effective transmission of such energy waves.

The assembly described above is normally supported by or carried on a wheeled cart so that operators can easily maneuver the probe, sheath and later the sheathed probe about.

FIG. 2 illustrates general steps 20 of sheathing a medical probe according to the prior art using an apparatus like the one illustrated in FIG. 1. Sterile gloves (sometimes called personal protective equipment or PPE) are donned by the operator at step 200. The operator removes the sheath from its packaging and holds it open at step 202, usually by grasping the collapsed sheath in one hand and using the second hand to create a crater-like inverted opening therein. The operator then squeezes an amount of sterile gel into the inverted opening of the sheath. This step must be done while holding the opened inverted sheath, so it can be awkward to perform with one hand, especially if the operator forgets to tear open or stage the gel dispenser or packet in advance. Additionally, this sheath lacks a clear orientation to assist the user in applying it. Any mistakes in grasping items by the operator during this procedure can lead to inadvertent breach of sterility. Also, the gel must be sterile since the user has donned his or her PPE at this time. The operator then must grasp the probe tip through the sheath while maintaining sterility at step 206. The sheath is unfurled, usually with the aid of a second operator or assistant at step 208. Steps 206 and 208 are particularly susceptible to breaches of sterility, especially if the operators are not highly expert at the procedure, which leads to increased risk of contamination and infection. Step 206 is typically a two-person operation, which leads to inefficiency, delay, and added liability and operating costs to the clinic and its patients.

A modern hospital can utilize between ten thousand and twenty thousand probe sheathing kits annually. With thousands of such hospitals and clinics in operation in the United States, it can be appreciated that effective, safe and economical sheathing devices and methods are of great use to the medical industry and the general public.

The present inventors have recognized a number of shortcomings of existing systems and methods for sheathing medical probes to which the following disclosure is directed.

SUMMARY

The present disclosure describes novel systems and methods for sheathing a medical probe. In various aspects, the present systems and methods provide: portability and compact design; ensure sterility of medical environments and probes; are injection moldable; allow for single-user operation; cover 1 meter or more of cabling for a probe; require minimum training and dexterity to operate; are compatible with multiple probe types; maintain a gel layer between the probe and its sheath; are significantly faster to deploy; support conventional packaging and sterilization methods; and support economical flat packing with minimal storage footprint.

Accordingly, one embodiment is directed to a system for applying a sterile sheath to a medical probe, comprising a probe holder comprising a housing having an exterior surface having at least one mechanical coupling, and said housing having an interior surface capable of supporting said medical probe; and a sheath shell configured and arranged to mechanically couple to said mechanical coupling on said probe holder, said sheath shell further being coupled to said sterile sheath.

Another embodiment is directed to a method for applying a sterile sheath to a medical probe, comprising securing said medical probe in a probe holder apparatus; unfolding a folded sheath shell attached to an open end of said sterile sheath; securing said sheath shell to said probe holder by wrapping said sheath shell about an exterior surface of said probe holder at one end of said sheath shell; pulling said medical probe from the outside of said sterile sheath at a closed end of said sterile sheath, said closed end of said sheath containing a tip of said medical probe and being opposed to said open end of the sterile sheath; extending said sheath to its full length with said medical probe therein; disconnecting said sheath from said sheath shell once the sheath is extended; and disposing of said sheath shell once said medical probe is enclosed in said sterile sheath.

IN THE DRAWINGS

Various embodiments of this invention are described below with reference to the accompanying drawings, in which.

Figure 5:
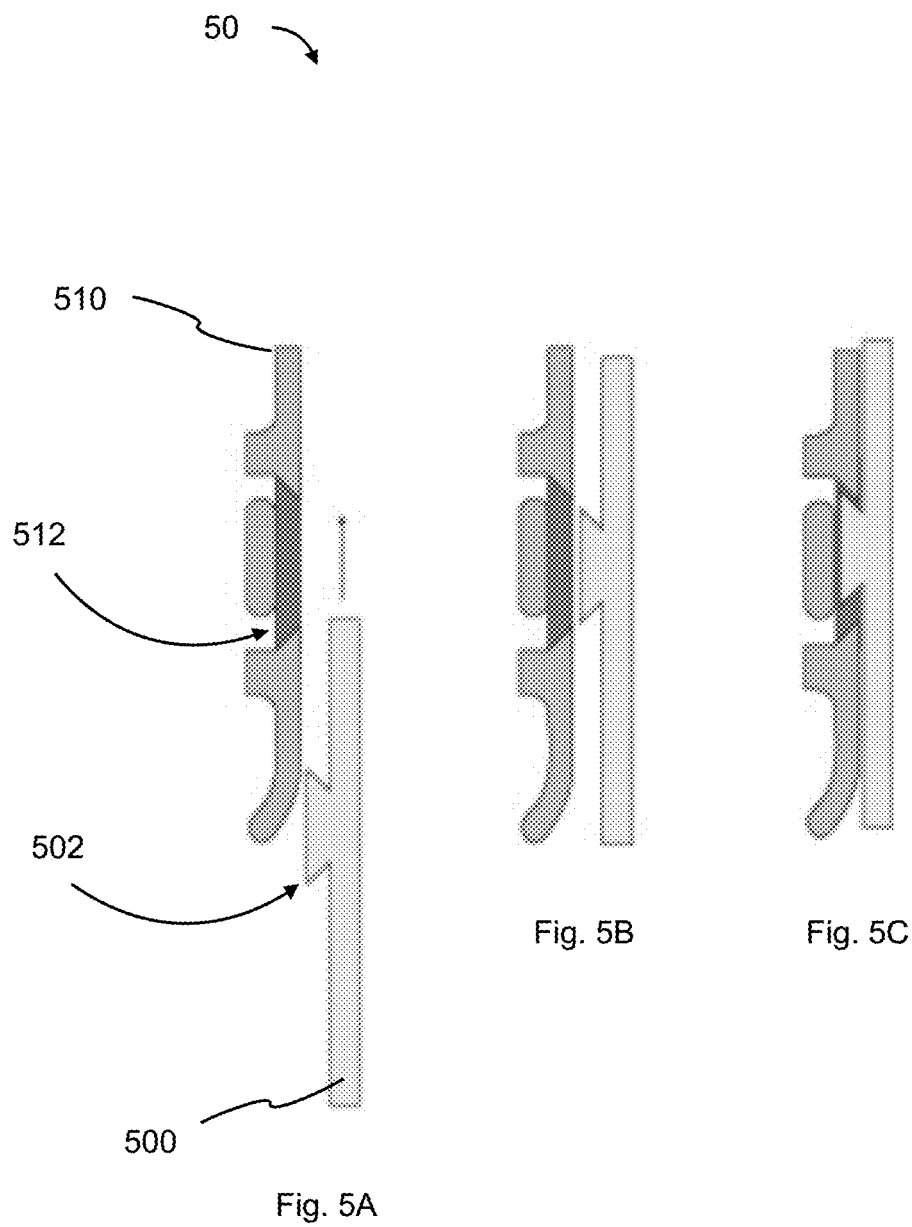
Figure 6:
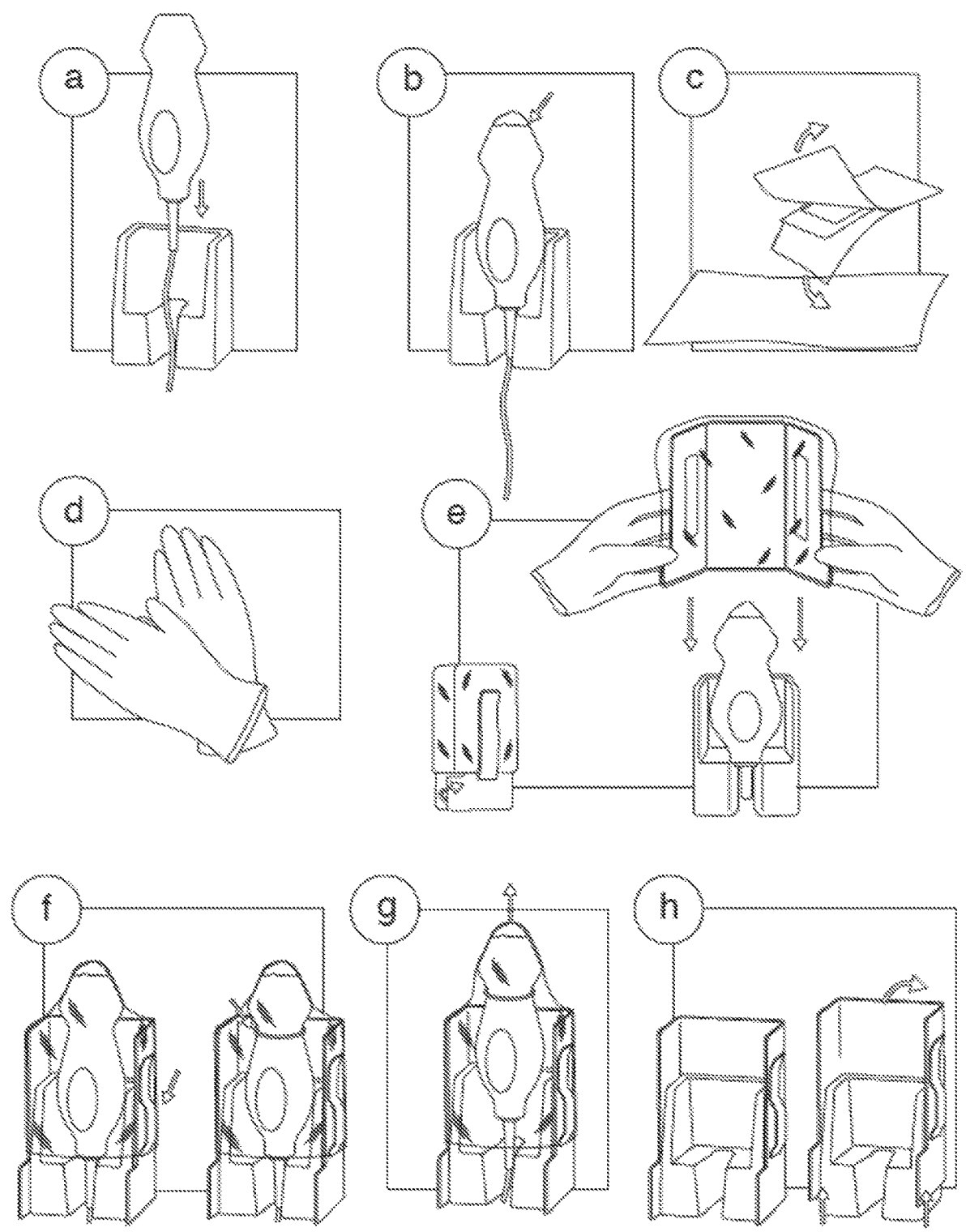
Figure 7:
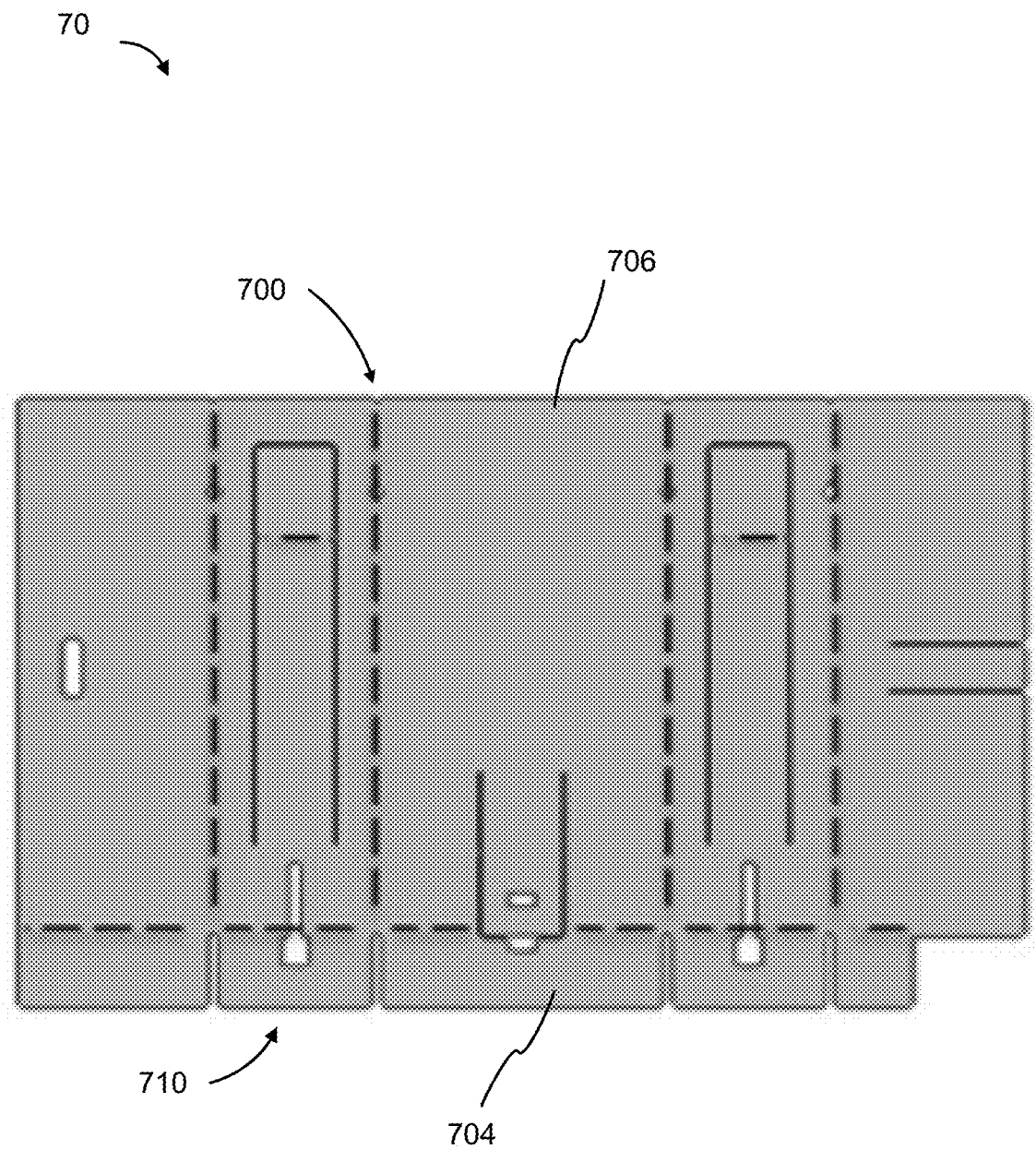
Figure 8:
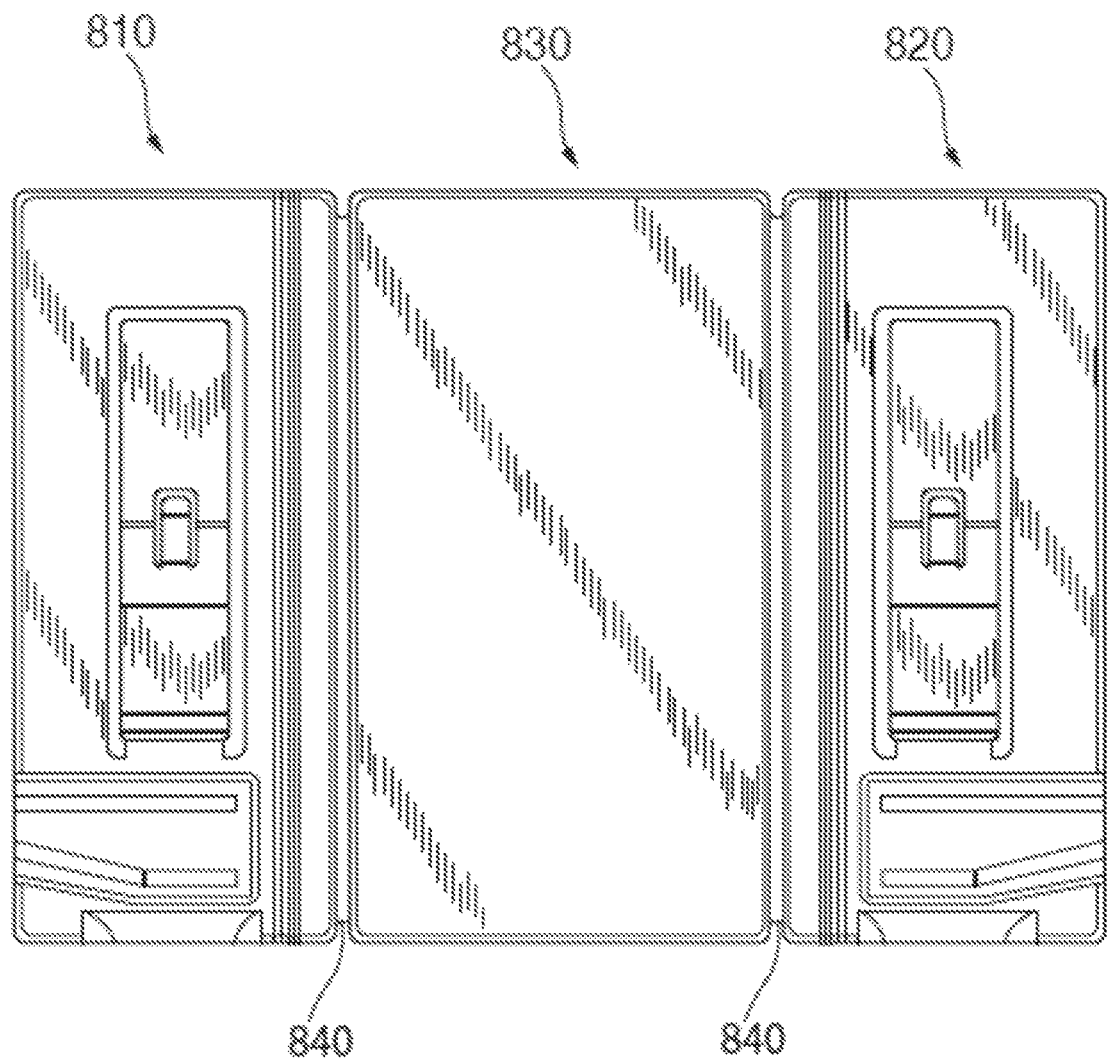
Figure 9:
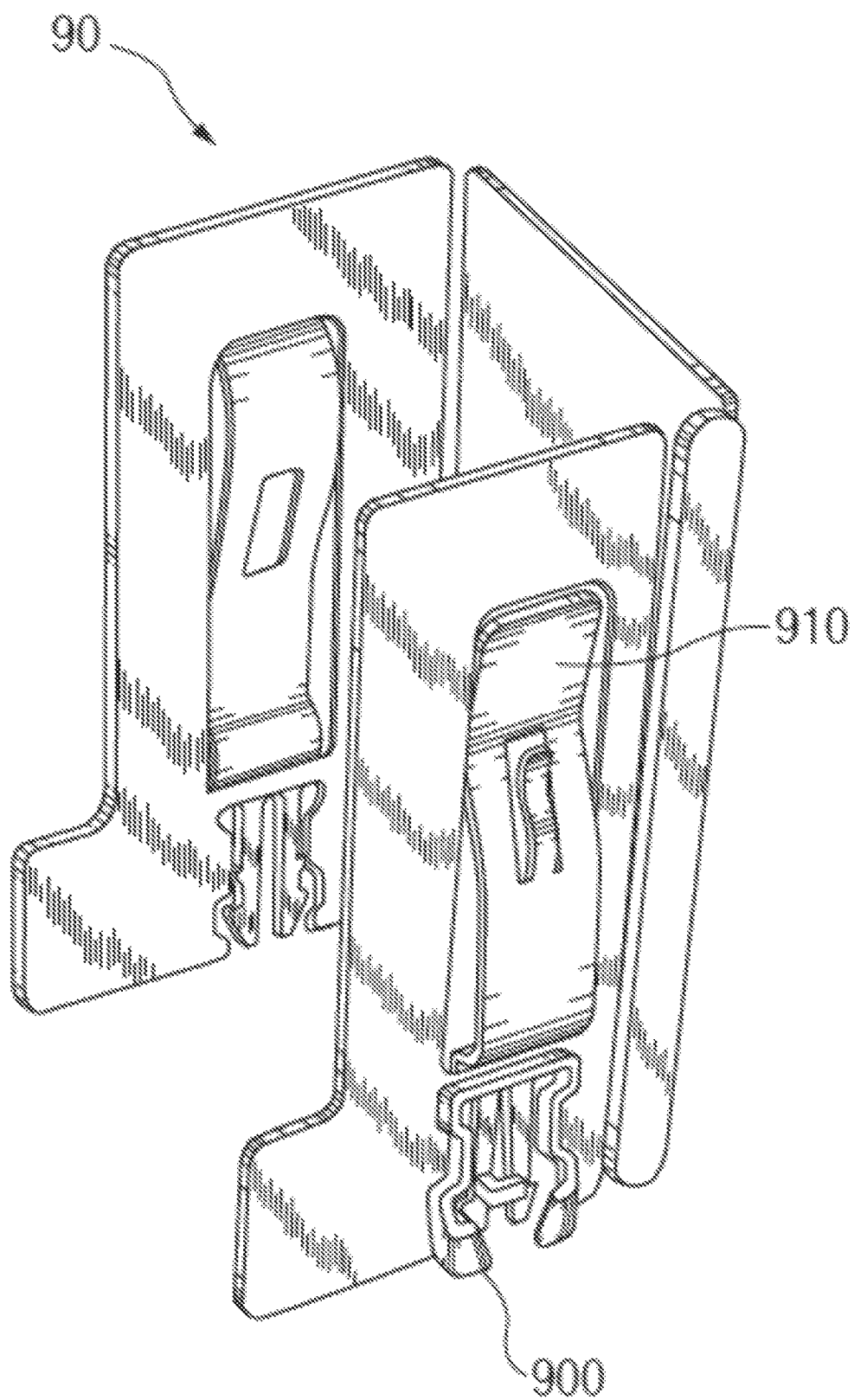

FIG. 5A, FIG. 5B, and FIG. 5C illustrate a cross sectional view of a fastener detail;

FIG. 6 illustrates illustrated instruction steps for applying the sterile sheath to a medical probe;

FIG. 7 illustrates a flattened sheath shell;

FIG. 8 illustrates a tri-fold formed sheath shell;

FIG. 9 illustrates another view of an exemplary sheath shell; and

Figure 10:
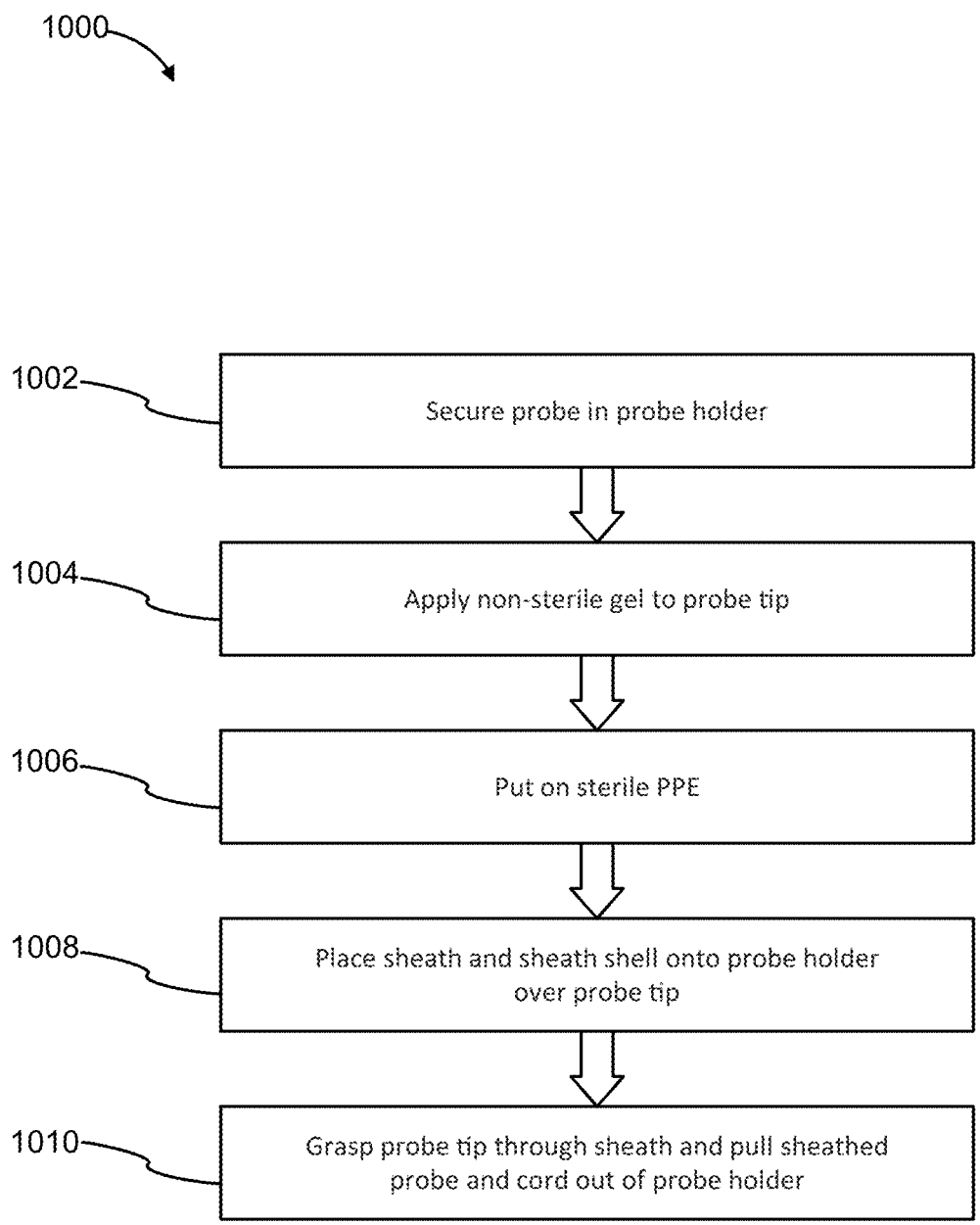

FIG. 10 illustrates steps of a method for sheathing a medical probe.

DETAILED DESCRIPTION

Aspects of the present disclosure are directed to a system for sheathing a medical probe as mentioned above. The system includes several primary components, to which those skilled in the art could add other components, substitutions, auxiliary attachments, and so on. The following descriptions of some preferred embodiments should not be read to exclude such other embodiments that would reasonably be appreciated within the overall invention and present disclosure. Therefore, the present illustrative discussion is not intended to be exhaustive of every scenario and apparatus conceivable under the invention. Furthermore, the present illustrations are not necessarily limiting in their geometric configurations, nor are they intended to be to scale for a given application, which will vary from one procedure or probe apparatus to another.

The system being described generally includes a probe holder for holding or supporting a medical probe and a sheath shell that is attached to the flexible sterile sheath at one end and mechanically coupleable to the probe holder at another end. The user just secures the probe in the probe holder, opens up the folded sheath shell and connects it to the probe holder to enable the grasping and pulling out of the probe, unfurling the flexible sheath on the probe for clinical use.

Figure 1:
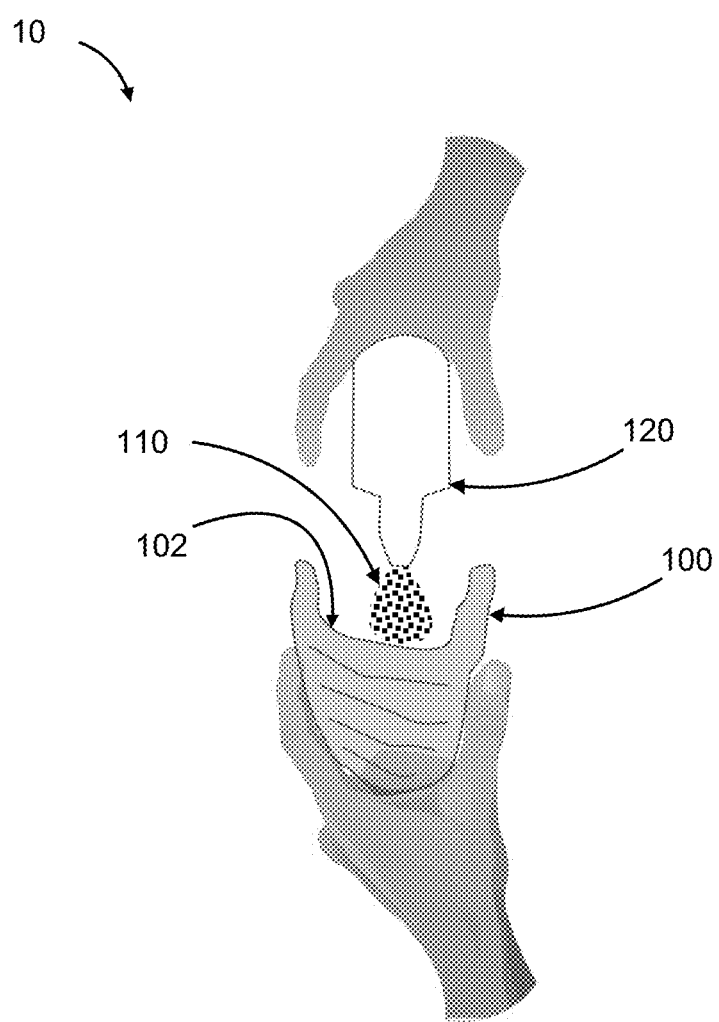
FIG. 1 illustrates a conventional non-sterile probe sheath according to the prior art.
Figure 2:
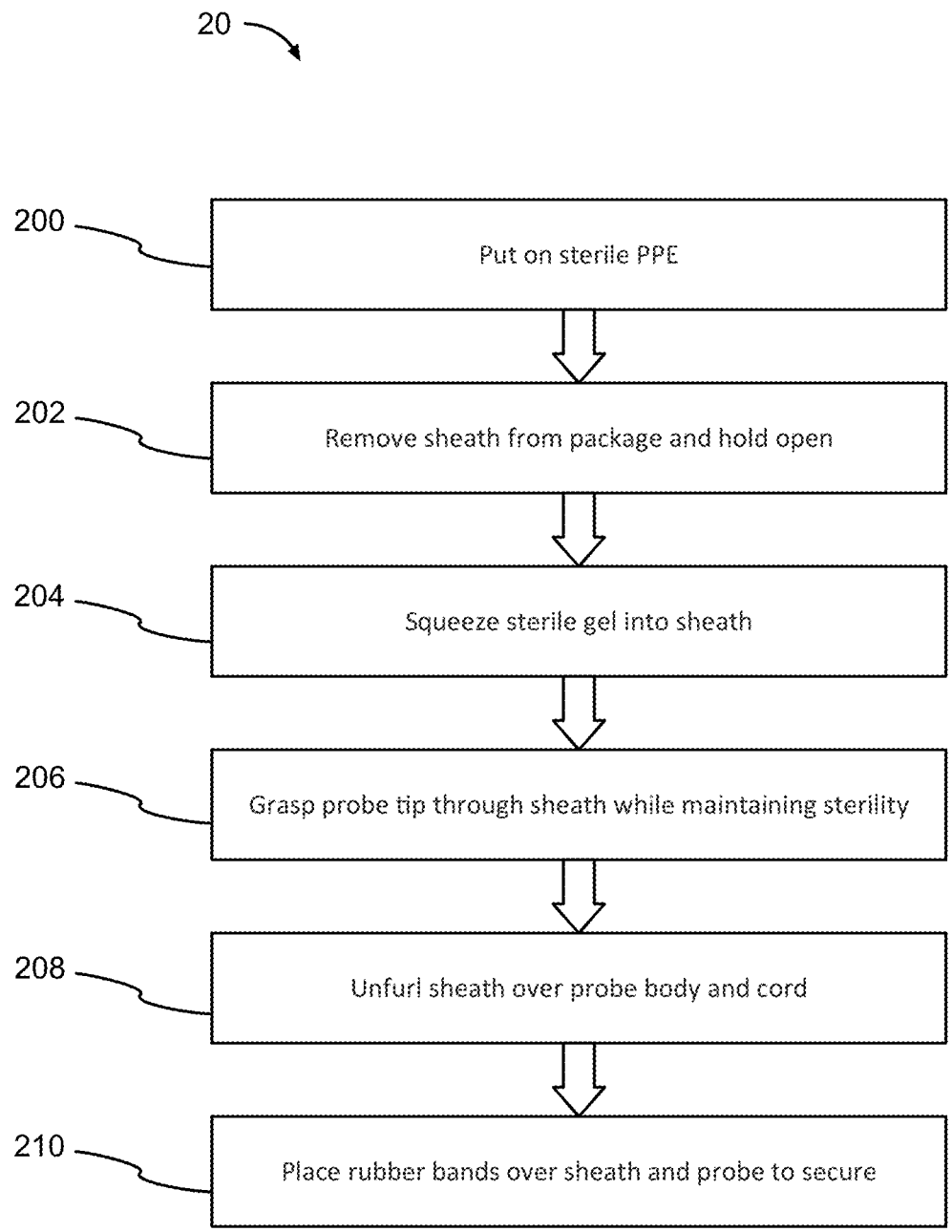
FIG. 2 illustrates steps of applying a sterile sheath to a medical probe according to the prior art.
Figure 3:
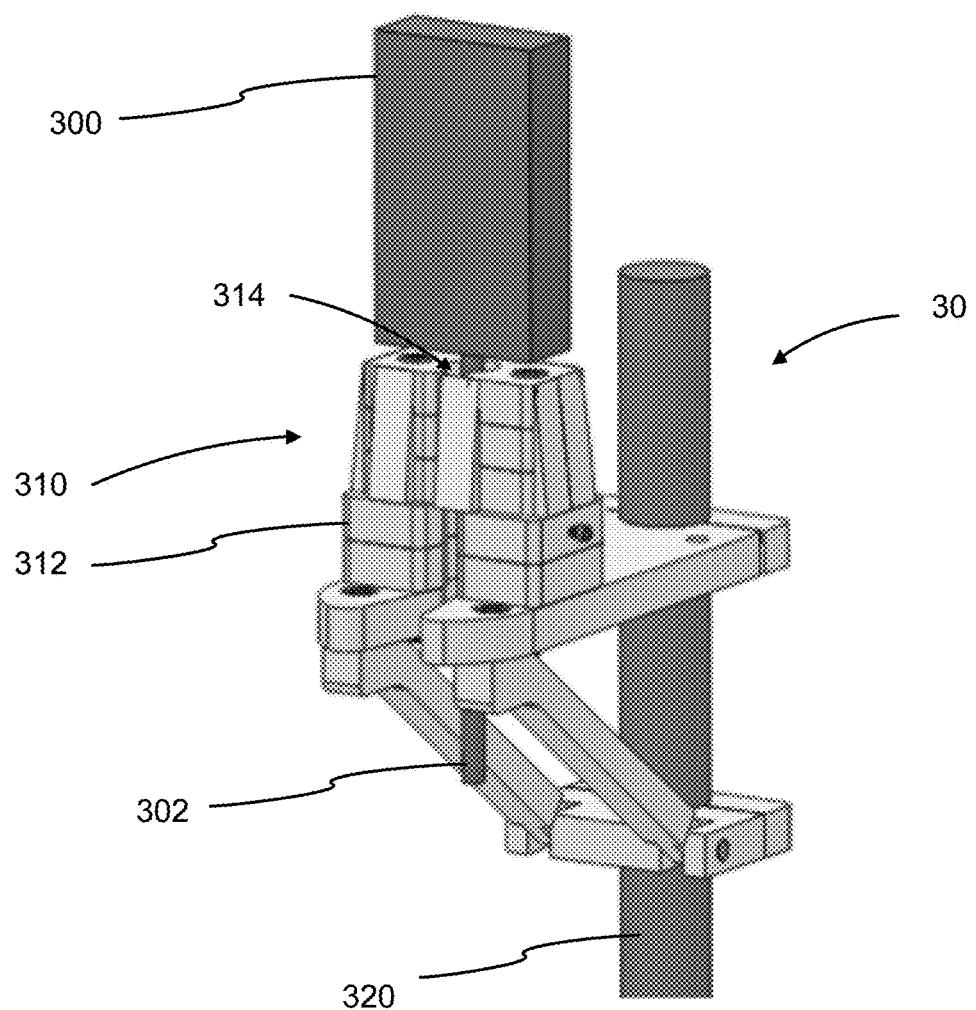
FIG. 3 illustrates a probe holder, generally.

FIG. 3 illustrates an exemplary probe holder 30 with a probe symbolized therein. The probe holder 30 includes a housing or body 310 that holds probe 300 in place (e.g., vertically with its tip pointed upwardly) during the sheathing operation. The probe housing comprises an outer surface 312 and an inner surface 314 in contact with the probe 300 and defining an interior volume or cavity in which probe 300 sits. The probe holder housing 310 may be closed, as shown in this example, or open in its design. The probe holder 30 may also be articulated to open and close about probe 300, and/or it may be articulated to be adaptable to holding various sizes and shapes of probes. An electrical cord, cable or connector 302 generally extends from the bottom of the probe, and the probe holder 30 has a channel, groove or other accommodation for passage of the cable 302. The probe holder can be positioned and supported by way of a support shaft 320 in some instances. The support shaft can be integrated with an ultrasound cart in some examples. Other probe holder designs will be referred to below, and it is intended that this component be general in nature to suit the application at hand and the type of probe and sheath being applied to it.

Figure 4:
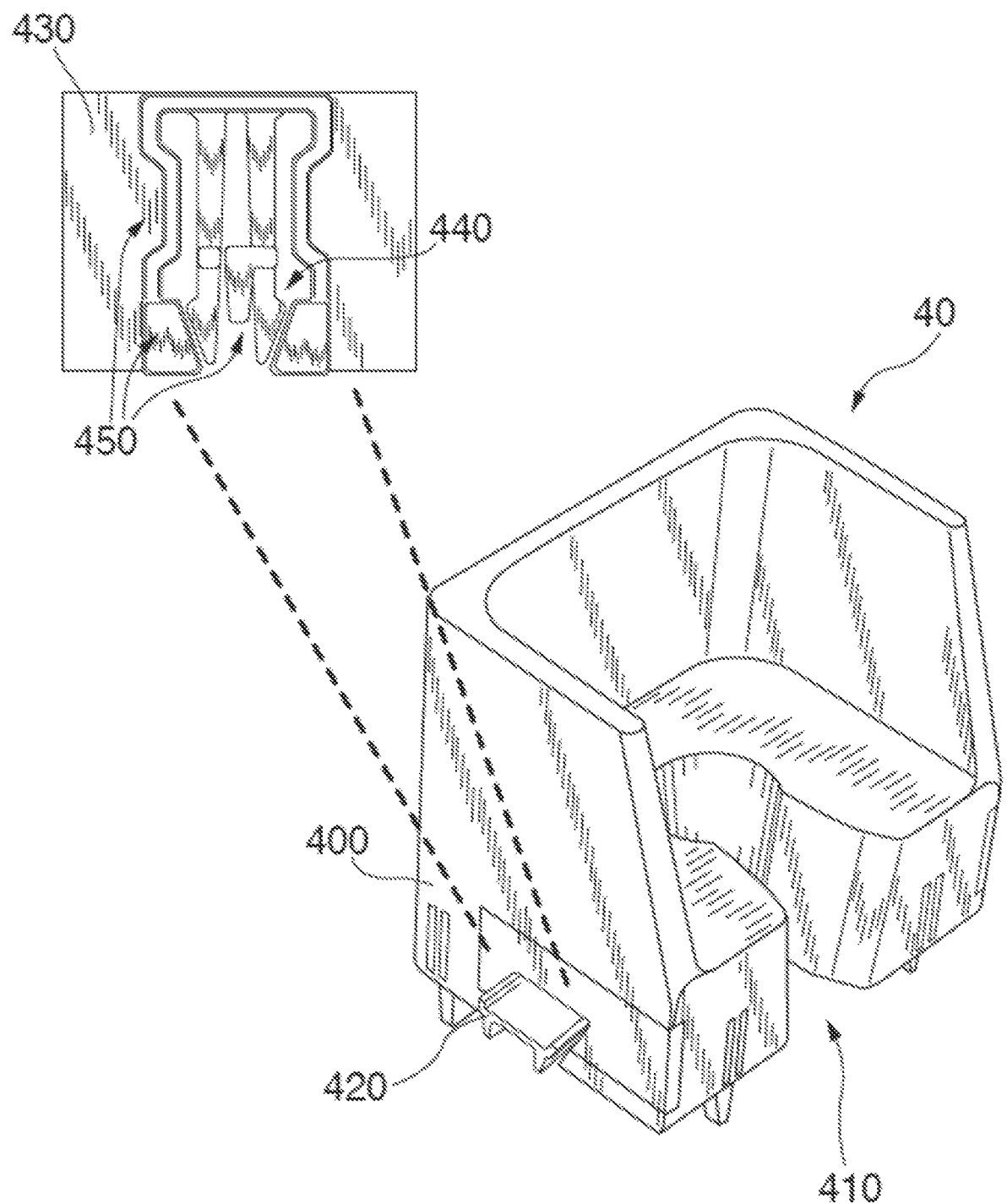
FIG. 4 illustrates an exemplary probe holder and fastener detail.

FIG. 4 illustrates another embodiment of a probe holder 40. The probe holder can be injection molded, cast, machined, or made from multiple parts. The probe holder may be made of a polymer generally, plastic, rubber, or metal. It includes a housing with an outer surface 400 and an inner surface in which the probe is placed. The inner surface can define an opening 410 or cavity for placement of the probe, which can also accommodate the probe's electrical cord therethrough. The probe holder also includes mechanical coupling points, detents, clips, snap-fit connectors, hooks, adhesive strips, tabs or other attachment means 420 to which the sheath shell can be coupled as will be described below. The drawing also conceptually illustrates the mating snap fittings 430 that are used in an embodiment to secure, by way of bendable connection inserts 440, the sheath shell (not shown) to the probe holder's mechanical couplings 420. Male-female parts of various kinds as appreciated by those skilled in the art may be used. Note that in some aspects sterility guards 450 may be employed to further reduce the risk of contamination of the sterile parts of the system.

FIGS. 5A-C illustrate an exemplary method for mechanical coupling or securement of the probe holder (not shown) with the sheath shell (not shown) by way of interlocking but disconnectable fasteners 500, 510. A protrusion, tab, tooth, or pin 502 will engage into a mating detent or recess 512 when the sheath shell is pushed onto the probe holder. In some embodiments, the connection is achieved by the spring loading force of the semi-flexible material from which the sheath shell is made (e.g., a semi hard plastic). In other embodiments, the attachment is achieved using dovetail shaped protrusions or a mortise and tenon architecture. In still other embodiments, a tab and complementary hood engagement clasp are used to achieve the connection between the body of the sheath shell and the outer surface of the probe holder assembly.

FIG. 5A shows the parts upon approach to one another. FIG. 5B shows the parts upon reaching their respective connection positions. And FIG. 5C shows the snap fit tab 502 mated to the corresponding detent 512 so that the parts are securely held in place during the sheathing of the probe. Of course, those skilled in the art can employ similar or equivalent fasteners to achieve a given objective without departure from the present technique or design and within the scope of this invention. For example, hook-and-loop, snaps, clasps, temporary rivets, adhesive strips, or other methods can be employed to couple the inside surface of the sheath shell to outside surface of the probe holder assembly.

FIG. 6 illustrates schematically a set of steps or instructions used to instruct a user on the method for using the present probe sheathing system. At Frame 6(a) the user is instructed to place the probe into the probe holder. Here, an ultrasound imaging probe or similar instrument has a probe tip at its upper end, which will remain upright and protruding from the probe holder. At its lower end the probe has an electrical or signaling cable that carries electrical driving power to the transducers in the probe tip and carries back sensed signals to an ultrasound imaging apparatus. The probe holder is shaped and sized to accommodate the probe and its cord, which are held in a cavity formed on the interior of the probe holder as described earlier. Gravity and friction fit are sufficient to secure the probe in the probe holder in some embodiments.

Frame 6(b) illustrates a dab of coupling gel (e.g., ultrasound coupling gel) placed on top of the probe tip. The gel may be non-sterile because the user has not committed to the sterile phase of the operation in donning his or her PPEs yet. However, of course, sterile gel may be used here as well for added measure. In Frame 6(c) the user tears open a sterile packet containing the sheath and the sheath shell, which are typically connected to each other at the open end of the sheath and at one end of the sheath shell. The sheath shell and the flexible sheath are optionally stowed in a collapsed form, which saves space and allows for flat packing of the sheath and sheath shell in a sealed package.

The user is instructed to put on the PPE at Frame 6(d). In this case the PPEs comprise sterile nitrile or similar surgical grade disposable gloves. At Frame 6(e) the user unfolds the multi-sided folded sheath shell and lowers it onto the probe holder so that the inside of the opened sheath shell and the outside of the probe holder slide against each other and so that the mechanical connection points of the sheath shell mate to those of the probe holder as described previously. The sheath shell and probe holder are secured to one another and the flexible sheath material is brought into contact with the probe tip and gel at Frame 6(f). Also, optionally, a rubber band can be applied around the probe tip on the outside of the sheath so that the probe tip remains securely placed inside the closed end of the sheath.

Now the probe may be grasped from its tip and pulled up and out of the probe holder at Frame 6(g), which causes the folded, collapsed flexible telescoping or accordioned sheath to unfurl along the length of the probe and its cord according to the length of the sheath. When the sheath is fully extended or unfurled it is automatically disconnected from its sheath shell and the sheath shell is left on the probe holder until it is unclipped from the probe holder at Frame 6(h). The sheath shell is then discarded and the probe holder is ready to receive another sheath shell.

FIG. 7 illustrates an exemplary sheath shell 70. The sheath shell may be made of a thin foldable material such as polymeric sheet material. In an aspect, the sheath shell is stamped from a larger sheet of such material, and tabs 710 and fold lines 700 are created therein by processes understood to those skilled in the art of manufacturing. The sheath shell 70 is preferably made sufficiently thin so that it can be folded into a flat pack packaging when stowed prior to use to save space. Also, the sheath shell 70 is preferably made of a semi-flexible material having sufficient rigidity to support its shape in the open deployed configuration when it is attached to the probe holder. Several materials can be used for making the sheath shell, and those skilled in the manufacturing art will appreciate the thickness of each material so that it satisfies the present objectives. In other aspects, the sheath shells are made to be stackable.

In yet other aspects, the sheath shells are configured to have multiple sides when in use. For example, the sheath shells can be in the shape of a tri-folded card when open, which substantially form three sides of a rectangle. According to an aspect, live hinges are stamped into the sheath sheet to allow for easy and guided folding of the sheath sheet when in use. In other embodiments, the sheath shell can have four sides, having a substantially rectangular cross section. The sheath shell has a wall height sufficient to allow a first removable connection to the probe holder at one end of the sheath shell and a second removable connection to the open end of an elongated flexible probe sheath at a second end of the sheath shell. The ends of the sheath shell that connect to the probe holder and the sheath material are generally at opposing edges 704, 706 of said sheath shell, which also act as sterility guards in some embodiments.

FIG. 8 illustrates another exemplary stamped and foldable multi-sided sheath shell 80. The sheath shell 80 comprises a center panel 830 and two side panels 810 and 820. A plurality (e.g., three) of live hinges 840 comprising a machined or a stamped reduced thickness groove allows for easy guided and precise folding of the sheath shell 80 to fit over a rectangular bodied probe holder. The missing side of the rectangle (the non-existent side opposing center panel 830) allows the sheath shell to remain open on one side to accommodate insertion and removal of the probe and its electrical cable into and out of the probe holder, usually at a face where the probe holder is also left open to accept the cable. Other securement clips, sterility barriers and various stamped features can be added to the sheath shell 80 as required to suit a particular application.

FIG. 9 illustrates an exemplary sheath shell structure 90. The sheath shell 90 includes tabs and other features to removably secure it to the probe holder (at clips 900) and to removably secure it using clips 910 to the open end of the sheath (not shown). The vertical tabs allow holding of the sheath in place with a suitable amount of force. In some embodiments, the corners of the semi-flexible sheath shell 90 are rounded to reduce the risk of tearing the thin membrane of the sheath material. In another aspect, rubber band tabs can be supplied to facilitate the grasping of the components. In addition, a pair of standoff thumb tabs can be provided on the outside of the sheath shell side walls so the operator can more easily guide the same onto the probe holder assembly and maintain the same in an opened configuration.

FIG. 10 illustrates basic steps of a method 1000 for applying a sterile flexible sheath to a medical probe. At step 1002 the medical probe is secured within the probe holder. At step 1004 a gel, e.g., a sterile or non-sterile gel, is applied to the tip of the medical probe if necessary. At step 1006 the user dons his or her sterile PPEs, e.g., surgical gloves. At step 1008 the user places the sheath shell over the probe and the probe holder so that the inside of the closed end of the collapsed flexible sheath is in contact with the gel and the probe tip. And at step 1010 the user grasps the sheathed probe tip from the outside of the sheath covering said probe tip and pulls the sheathed probe tip up and out of the probe holder, unfurling the remainder of the flexible sheath over the rest of the probe's body and its electrical cable. This procedure maintains sterility and only requires one person to perform.

The result of the above process and system is that medical probes can be more easily and economically sheathed prior to sterile use in a clinical setting. The materials required (e.g., a sheath kit) would include the folded or furled sheath and the sheath shell, which is a multi-folded plastic assembly that is opened at the time of use to couple to both a probe holder and to the sheath material. Once the probe is fully sheathed, the sheath is disconnected from the sheath shell and the sheath shell can be discarded.

The present invention should not be considered limited to the particular embodiments described above, but rather should be understood to cover all aspects of the invention as fairly set out in the attached claims. Various modifications, equivalent processes, as well as numerous structures to which the present invention may be applicable, will be readily apparent to those skilled in the art to which the present invention is directed upon review of the present disclosure. The claims are intended to cover such modifications and equivalents.

What is claimed is:

1. A system for sterile containment of a medical probe, the system comprising:
    a sterile sheath comprising a flexible polymer sleeve, the flexible polymer sleeve having an open end and a closed end, the open end to receive said medical probe;
    a sheath shell coupled to said sterile sheath, the sheath shell disposed relative to said sterile sheath to shape said open end of said sterile sheath to receive said medical probe;
    a probe holder including a housing having a cavity defined therein to support to the medical probe;
    a first fastener disposed on an outer surface of the housing of the probe holder or on an inner surface of the sheath shell, the first fastener comprising a protrusion, a tab, a tooth, or a pin;
    a second fastener comprising a mating detent or recess, the second fastener (a) disposed on the outer surface of the housing of the probe holder when the first fastener is disposed on the inner surface of the sheath shell or (b) disposed on the inner surface of the sheath shell when the first fastener is disposed on the outer surface of the housing of the probe holder,
    wherein the first and second fasteners comprise interlocking but disconnectable fasteners.

2. The system of claim 1, wherein said sheath shell is attached to said sterile sheath at said open end of said sterile sheath.

3. The system of claim 1, wherein said sheath shell is attached to a portion of said sterile sheath that is not at said open end of said sterile sheath.

4. The system of claim 1, wherein the sheath shell is fabricated separately from said sterile sheath.

5. The system of claim 1, wherein said sheath shell has a radially outer surface and said sterile sheath includes a portion: (a) disposed radially outward of said radially outer surface of said sheath shell and/or (b) in physical contact with said radially outer surface of said sheath shell.

6. The system of claim 1, wherein said sheath shell is graspable, directly and/or indirectly through the sterile sheath, and movable by a user to move said open end of said sterile sheath relative to said medical probe.

7. The system of claim 1, wherein said sterile sheath has a longitudinal axis and said sheath shell is disposed about said longitudinal axis.

8. The system of claim 7, wherein said sheath shell extends: (a) substantially 270 degrees around said longitudinal axis of said sterile sheath and/or (b) substantially 360 degrees around said longitudinal axis of said sterile sheath.

9. The system of claim 1, wherein said sheath shell is made of: (a) a semi-flexible material, (b) a semi-flexible material that provides a spring loading force and/or (c) a semi hard plastic.

10. The system of claim 1, wherein said sheath shell comprises live hinges that allow for guided folding of the sheath shell.

11. The system of claim 1, further comprising: (a) a sealed package within which are disposed said sterile sheath and said sheath shell and/or (b) a sterile packet within which are disposed said sterile sheath and said sheath shell.

12. The system of claim 11, wherein said sealed package is openable.

13. The system of claim 11, wherein said sealed packet is tearable to open the sealed packet.

14. The system of claim 1, wherein said sheath shell has a rigidity that is greater than that of said sterile sheath.

15. The system of claim 1, wherein said sheath shell has sufficient rigidity to support its shape.

16. The system of claim 1, wherein said flexible polymer sleeve is an elongated flexible polymer sleeve in a non-extended configuration.

17. The system of claim 16, wherein said elongated flexible polymer sleeve is in a: (a) folded configuration, (b) collapsed configuration, (c) accordioned configuration and/or (d) furled configuration.

18. The system of claim 1, wherein said flexible polymer sleeve is an elongated flexible polymer sleeve, wherein said elongated flexible polymer sleeve is a telescoping sleeve in an untelescoped configuration.

19. The system of claim 1, further comprising gel disposed on an interior surface of said closed end of said sterile sheath.

20. The system of claim 19, further comprising said medical probe, wherein said gel is disposed between said medical probe and said interior surface of said closed end of said sterile sheath.

21. A method for applying a sterile sheath to a medical probe, comprising:
    providing said system of claim 1;
    mechanically engaging the sheath shell portion of the system with the probe holder holding said medical probe by engaging the first and second fasteners; and
    providing relative movement between said system and said medical probe to cause said medical probe to be received in said open end of the sterile sheath.

22. The method of claim 21, further comprising extending said sterile sheath with said medical probe therein.

23. A system for sterile containment of a medical probe, the system comprising:
    a sterile sheath comprising an elongated flexible polymer sleeve, the elongated flexible polymer sleeve having an open end and a closed end, the open end to receive said medical probe; and
    a sheath shell separate from said medical probe and coupled to said sterile sheath, the sheath shell having a shape and position in a deployable configuration relative to the sterile sheath to shape said open end of said sterile sheath to receive said medical probe;
    a probe holder including a housing having a cavity defined therein to support to the medical probe;
    a first fastener disposed on an outer surface of the housing of the probe holder or on an inner surface of the sheath shell, the first fastener comprising a protrusion, a tab, a tooth, or a pin;
    a second fastener comprising a mating detent or recess, the second fastener (a) disposed on the outer surface of the housing of the probe holder when the first fastener is disposed on the inner surface of the sheath shell or (b) disposed on the inner surface of the sheath shell when the first fastener is disposed on the outer surface of the housing of the probe holder, wherein the first and second fasteners comprise interlocking but disconnectable fasteners.

24. The system of claim 23, further comprising a plurality of said first or second fasteners, wherein said sheath shell comprises four sides in the deployable configuration; and wherein a plurality of said sides are provided with a respective one of said first or second fasteners.

25. The system of claim 23, wherein said sheath shell comprises a substantially rectangular cross section in the deployable configuration.

26. The system of claim 23, further comprising a plurality of said first or second fasteners, wherein said sheath shell comprises four sides and has a substantially rectangular cross section in the deployable configuration, said deployable configuration permitting opening a flat packed sheath shell to an open form that has said rectangular cross section and supports a plurality of said first or second fasteners on a plurality of faces of said rectangular cross section that mate with respective second or first fasteners, respectively, on said probe holder.

27. The system of claim 23, wherein said sheath shell is of sufficient rigidity to support its shape in the deployable configuration; and wherein the the first fastener further comprises any of: a plastic clip, a snap-fit tab, or a hook, and the second fastener further comprises a detent.

28. A method for applying a sterile sheath to a medical probe, comprising:

providing said system of claim 27;

locking said interlocking but disconnectable mechanical fasteners of the respective sheath shell and probe holder;

providing relative movement between said system and said medical probe to cause said medical probe to be received in said open end of the sterile sheath; and releasing said sheath shell from said probe holder once said medical probe is received in the sterile sheath.

* * * * *